(12) United States Patent
Hathorn

(10) Patent No.: US 10,624,808 B2
(45) Date of Patent: *Apr. 21, 2020

(54) METHOD AND APPARATUS FOR ENHANCED VISUALIZATION DURING ENDOSCOPY

(71) Applicant: ColoWrap, LLC, Durham, NC (US)

(72) Inventor: James Hathorn, Durham, NC (US)

(73) Assignee: COLOWRAP, LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/256,019

(22) Filed: Sep. 2, 2016

(65) Prior Publication Data

US 2017/0042752 A1    Feb. 16, 2017

Related U.S. Application Data

(63) Continuation-in-part of application No. 13/344,715, filed on Jan. 6, 2012, now Pat. No. 9,724,225, and a
(Continued)

(51) Int. Cl.
*A61F 5/00* (2006.01)
*A61B 17/00* (2006.01)
(Continued)

(52) U.S. Cl.
CPC ............. *A61H 1/008* (2013.01); *A61B 90/17* (2016.02); *A61F 5/0009* (2013.01); *A61F 5/03* (2013.01);
(Continued)

(58) Field of Classification Search
CPC ......... A61F 13/148; A61F 5/0009; A61F 5/03
See application file for complete search history.

(56) References Cited

U.S. PATENT DOCUMENTS 3,115,879 A    12/1963  Kaplan
3,120,846 A    2/1964   Fletcher
(Continued)

FOREIGN PATENT DOCUMENTS

CN    202161367 U    3/2012
GB    2 381 732 A    5/2003
(Continued)

OTHER PUBLICATIONS

European Search Report of related European Patent Application No. 12864172.7 dated Sep. 2, 2015.
(Continued)

*Primary Examiner* — Diane D Yabut
(74) *Attorney, Agent, or Firm* — Arent Fox LLP

(57) ABSTRACT

A method and apparatus for improving adenoma detection, including applying compression to the abdomen of a patient and maintaining compression of the abdomen of the patient during withdrawal of an endoscope. The compression may be applied by wrapping a band of elastic material around the abdomen of a patient and connecting one end of the band to another portion of the band to maintain tension in the band in order to apply compression to the abdomen of the patient. Aspects may also include tensioning the band prior to connecting the one end of the band to the another portion of the band to apply a desired degree of pressure to the patient's abdomen through contraction of the band across at least a portion of the patient's abdomen.

16 Claims, 16 Drawing Sheets

Related U.S. Application Data continuation-in-part of application No. 14/575,860, filed on Dec. 18, 2014, now Pat. No. 10,441,222.

(60) Provisional application No. 62/214,747, filed on Sep. 4, 2015, provisional application No. 61/944,658, filed on Feb. 26, 2014, provisional application No. 61/917,469, filed on Dec. 18, 2013.

(51) Int. Cl.
| | |
|---|---|
| A61H 1/00 | (2006.01) |
| A61F 5/30 | (2006.01) |
| A61B 90/17 | (2016.01) |
| A61F 13/14 | (2006.01) |
| A61F 5/03 | (2006.01) |
| A61F 5/26 | (2006.01) |

(52) U.S. Cl.
CPC .............. *A61F 5/30* (2013.01); *A61F 13/148* (2013.01); *A61B 2017/00818* (2013.01); *A61F 5/26* (2013.01); *A61H 2205/083* (2013.01)

(56) References Cited

U.S. PATENT DOCUMENTS

| | | |
|---|---|---|
| 3,554,190 A | 1/1971 | Kaplan |
| 3,902,503 A | 9/1975 | Gaylord, Jr. |
| 4,833,730 A | 3/1989 | Nelson |
| 4,991,234 A | 2/1991 | Greenberg |
| 5,188,585 A | 2/1993 | Peters |
| 5,489,260 A | 2/1996 | Striano |
| 5,647,824 A | 7/1997 | Levenson |
| 5,685,321 A | 11/1997 | Klingenstein |
| 5,820,575 A | 10/1998 | Cabrera et al. |
| 5,885,230 A | 3/1999 | Cherry |
| 6,672,311 B2 | 1/2004 | Rindfleish |
| 8,066,657 B2 | 11/2011 | Frazer |
| 2002/0108617 A1 | 8/2002 | Burton |
| 2011/0087263 A1 | 4/2011 | Arber |
| 2013/0178893 A1 | 7/2013 | Hathorn |
| 2014/0323802 A1* | 10/2014 | Lloyd .................. G09B 23/285 600/104 |

FOREIGN PATENT DOCUMENTS

| | | |
|---|---|---|
| JP | 3051938 U | 6/1998 |
| JP | 2005-021113 A | 1/2005 |
| JP | 2006-314711 A | 11/2006 |
| KR | 200264387 Y1 | 2/2002 |
| WO | WO 9508308 A1 | 3/1995 |
| WO | WO 9614811 A1 | 5/1996 |
| WO | WO 9746180 A1 | 5/1996 |

OTHER PUBLICATIONS

International Search Report and Written Opinion of related International Patent Application No. PCT/US2014/071218 dated Mar. 24, 2015.

Soper, Nathaniel J., et al., "Chapter 45: Flexible Endoscopy of the Lower Gastrointestinal Tract, Endoscopic and Laparoscopic Surgery," Lippinscott Williams & Wilkins, Philadelphia, PA, 2009, pp. 451.

\* cited by examiner

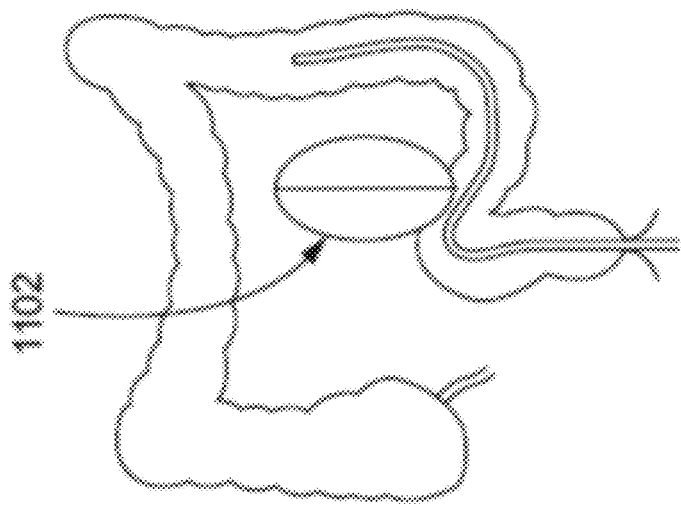
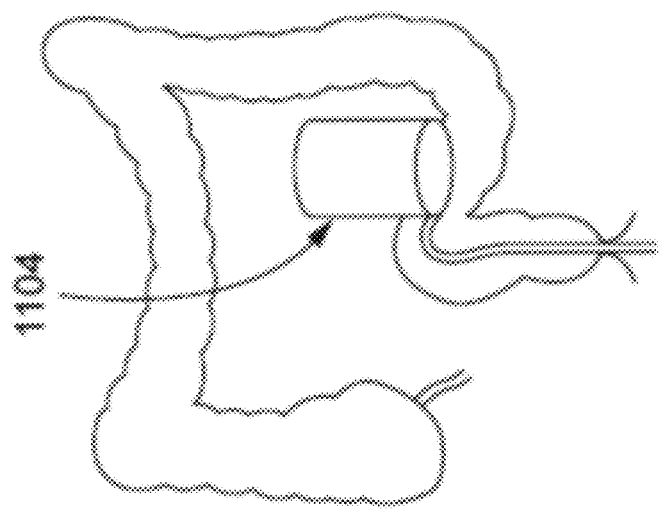
FIG. 10

METHOD AND APPARATUS FOR ENHANCED VISUALIZATION DURING ENDOSCOPY

CROSS-REFERENCE TO RELATED APPLICATION

This application is a continuation-in-part of U.S. application Ser. No. 13/344,715, entitled "METHOD AND APPARATUS FOR TENSILE COLONOSCOPY COMPRESSION," and filed on Jan. 6, 2012, now U.S. Pat. No. 9,724,225 and U.S. application Ser. No. 14/575,860, entitled "Endoscopy Band with Sigmoid Support Apparatus," and filed on Dec. 18, 2014, now U.S. Pat. No. 10,441,222 which claims the benefit of U.S. Provisional Application Ser. No. 61/917,469, entitled "COLONOSCOPY BAND WITH SIGMOID SPLINT" and filed on Dec. 18, 2013, and U.S. Provisional Application Ser. No. 61/944,658 entitled "ENDOSCOPY BAND WITH SIGMOID SUPPORT APPARATUS" and filed on Feb. 26, 2014, and claims the benefit of U.S. Provisional Application Ser. No. 62/214,747, entitled "IMPROVED BOWEL STABILITY AND ENHANCED VISUALIZATION DURING ENDOSCOPY" and filed on Sep. 4, 2015, the entire contents of each of which is expressly incorporated by reference herein in its entirety.

BACKGROUND

The human body is comprised of many different solid organs (such as the liver or spleen) and luminal systems (such as the gastrointestinal tract or the urinary tract.) In many cases, it may be desirable or necessary to examine, diagnose, and/or treat disease processes that are located within, or on the side wall of a body lumen or cavity. A colonoscopy procedure is an example of how one might examine a luminal structure.

The human body is comprised of many different solid organs (such as the liver or spleen) and luminal systems (such as the gastrointestinal tract or the urinary tract.) In many cases, it may be desirable or necessary to examine, diagnose, and/or treat disease processes that are located within, or on the side wall of, a body lumen or cavity. A colonoscopy procedure is an example of how one might examine a luminal structure.

Colonoscopy involves the use of a flexible inspection device which is inserted into the distal end of the colon (rectum) and is advanced to the start of the colon (cecum.) Once the cecum is reached, the scope is withdrawn in order to examine the terminal ileum, colon, and rectum. Inspection of the colon and therapeutic maneuvers are primarily performed during the when the scope is being withdrawn. In addition to polyps (and tumors if present), the presence of erythema, erosions, ulcers, diverticula, melanosis coli, hemorrhoids, and condyloma are noted. A variety of diagnostic and therapeutic maneuvers can be performed during colonoscopy. These include endoscopic hemostasis, dilation of colonic or anastomotic strictures, stent placement for malignant disease, endoscopic mucosal resection of gastrointestinal tumors, foreign body removal, placement of colonic decompression tube, percutaneous endoscopic cecostomy tube placement, and tissue sampling and removal of visible lesions (also known as polyps). Sampling and removal of polyps is the most common maneuver performed during the procedure.

Colonoscopy has become the gold-standard screening and prevention tool for colorectal cancer as a result of the fact that precancerous polyps (known as adenomas) can be identified and removed during the procedure. For example, adenomas may be detected when they are identified by physicians visually inspecting the interior lining of the colon during the withdrawal phase of the procedure. As a result, methods and devices for enhancing adenoma detection generally aim to improve visualization of the colon and colonic mucosa. In addition to patients successfully completing pre-procedure bowel preparation and physicians investing sufficient time and attention performing withdrawal, optimal visualization can be ensured by obtaining sufficient insufflation/distention of the lumen, visualizing the entire circumference of the colon, inspecting behind and in between colonic folds, repeatedly inspecting areas (especially around turns) by back and forth movement of scope, and by reducing colonic contractions during withdrawal. New technologies aiming to enhance adenoma detection include high definition endoscopes with visual image enhancement, endoscopes that permit a wider field of vision, and accessory devices that attach to the tip of the scope and permit visualization behind mucosal folds. New methods for improving adenoma detection recently described in the literature include training staff to look for adenomas (on the screen/monitor) alongside the physician, the use of water (in addition to or in place of air or CO2) to clean and distend the colon, and the use of antispasmodic medication to reduce colon spasms.

Numerous studies have found a significant relationship between improved detection of adenomas during colonoscopy and reductions in the incidence of colorectal cancer among patients having undergone the procedure. For example, in an examination of 314,872 colonoscopies performed by 136 gastroenterologists over a ten year period Corley et al found that each 1% increase in Adenoma Detection Rate (ADR) resulted in a 3% reduction in the incidence of colorectal cancer.[1] Accordingly, there is considerable need and demand for new technologies and methods that improve adenoma detection.

[1] Corley, et al. Adenoma Detection Rate and Risk of Colorectal Cancer and Death. New England Journal of Medicine. 2014; 370: 1298-1306.

SUMMARY

In an aspect of the disclosure, a novel method and apparatus is provided for improving visualization and enhancing adenoma detection during endoscopy.

The use of external abdominal compression to facilitate insertion and advancement of an endoscope into and through the bowel can be very important. The basis for the application of abdominal pressure during insertion is to support and provide counter-pressure to the colon to reduce the formation of loops that hinder the advancement of the scope to the cecum. This need is obviated, however, during the withdrawal phase as loops are naturally reduced by the motion of the scope being withdrawn from the body.

Aspects presented herein provide an improvement in visualization and adenoma detection ADR through the application of abdominal compression during the withdrawal phase of colonoscopy.

Aspects include providing broad, general lower abdominal compression during withdrawal of an endoscope in order to increase ADR. Additionally, aspects may include providing more substantial, focused compression to any of the left lower abdomen, left upper abdomen, right lower abdomen, right upper abdomen, right colon, left colon, cecum, ascending colon, hepatic flexure, transverse colon, splenic flexure, descending colon, sigmoid colon and rectum specifically.

BRIEF DESCRIPTION OF THE DRAWINGS

FIG. 10 illustrates example inserts for focused compression in accordance with aspects presented herein.

DETAILED DESCRIPTION

Figure 1:
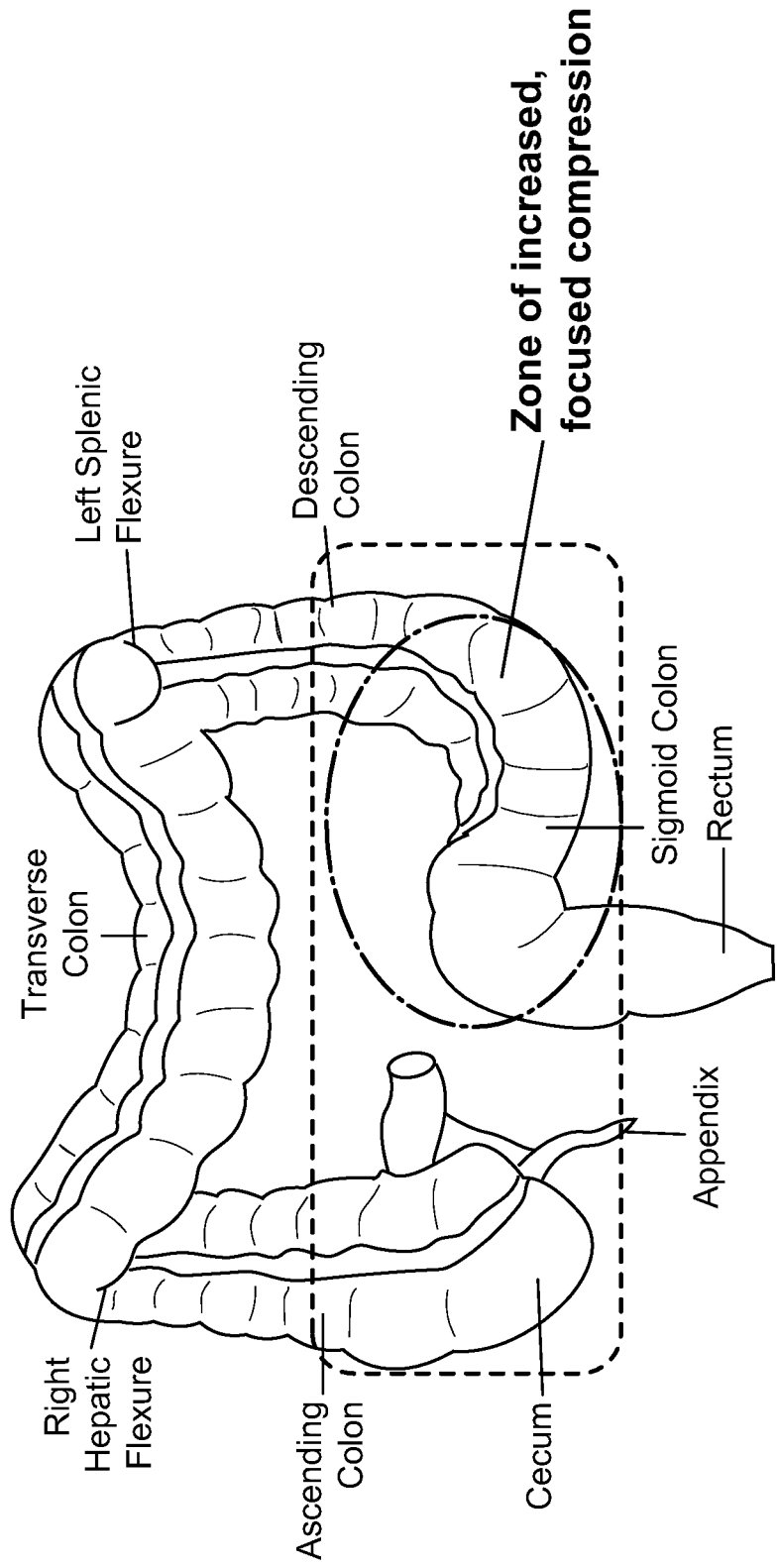
FIG. 1 illustrates an example zone of increased, directed compression that may be applied to the abdomen in accordance with aspects presented herein.

The detailed description set forth herein in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details and that the invention is not limited in its application to the details of construction and the arrangements of components set forth in the following description or illustrated in the drawings. Moreover, the claims hereof are not to be read restrictively unless there is clear and convincing evidence manifesting a certain exclusion, restriction, or disclaimer.

Example regions of the colon that may be impacted by the application of compression during withdrawal of an endoscope are indicated in FIG. 1. FIG. 1 illustrates an example zone of increased, directed compression that may be focused on the left colon and the sigmoid colon specifically.

Figure 2:
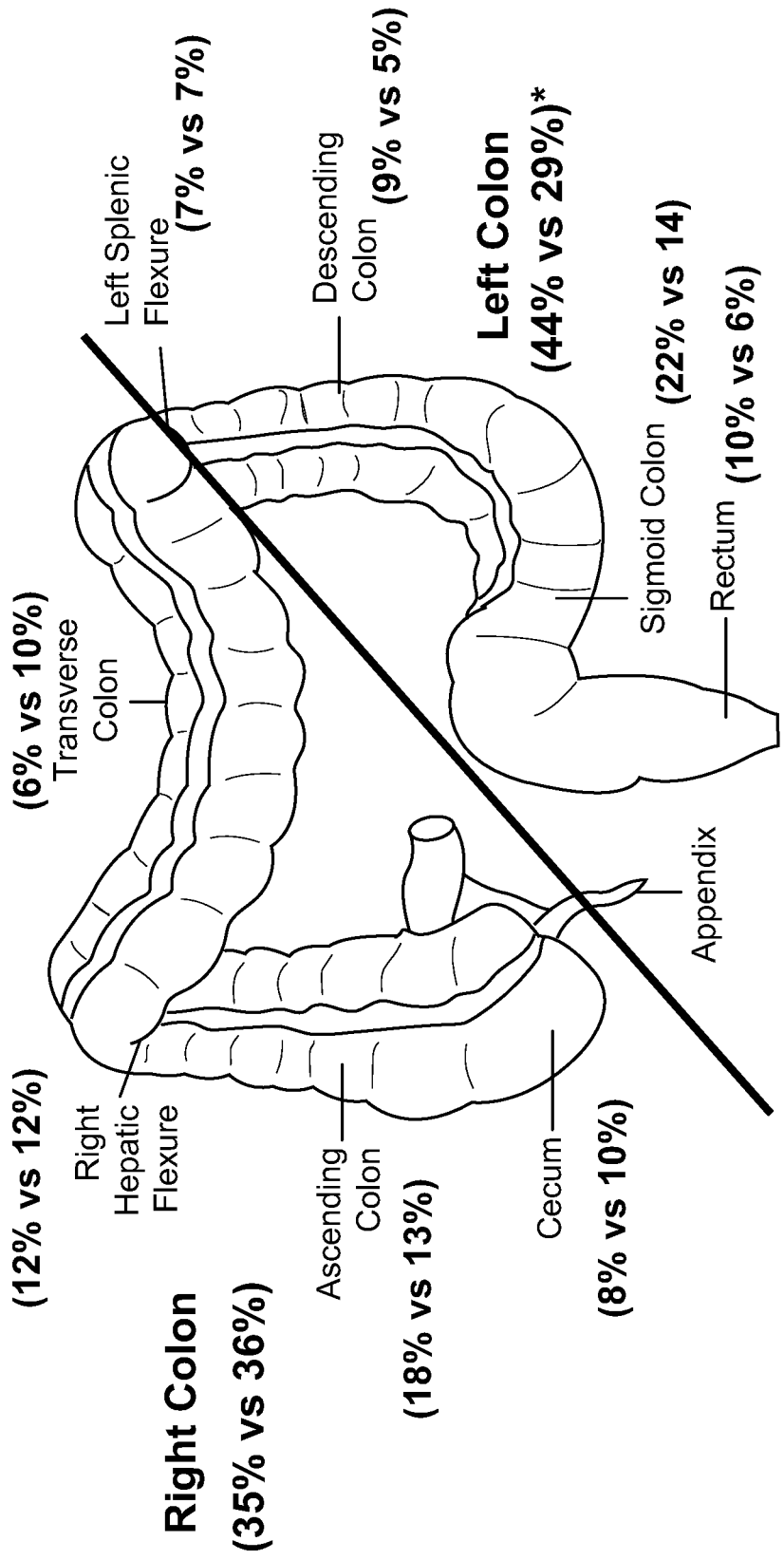
FIG. 2 illustrates examples of adenoma detection rate by location in accordance with aspects presented herein.

FIG. 2 displays the increase in adenoma detection rates between the treatment and the sham groups for each colon segment and for the left colon and the right colon generally.

Figure 3:
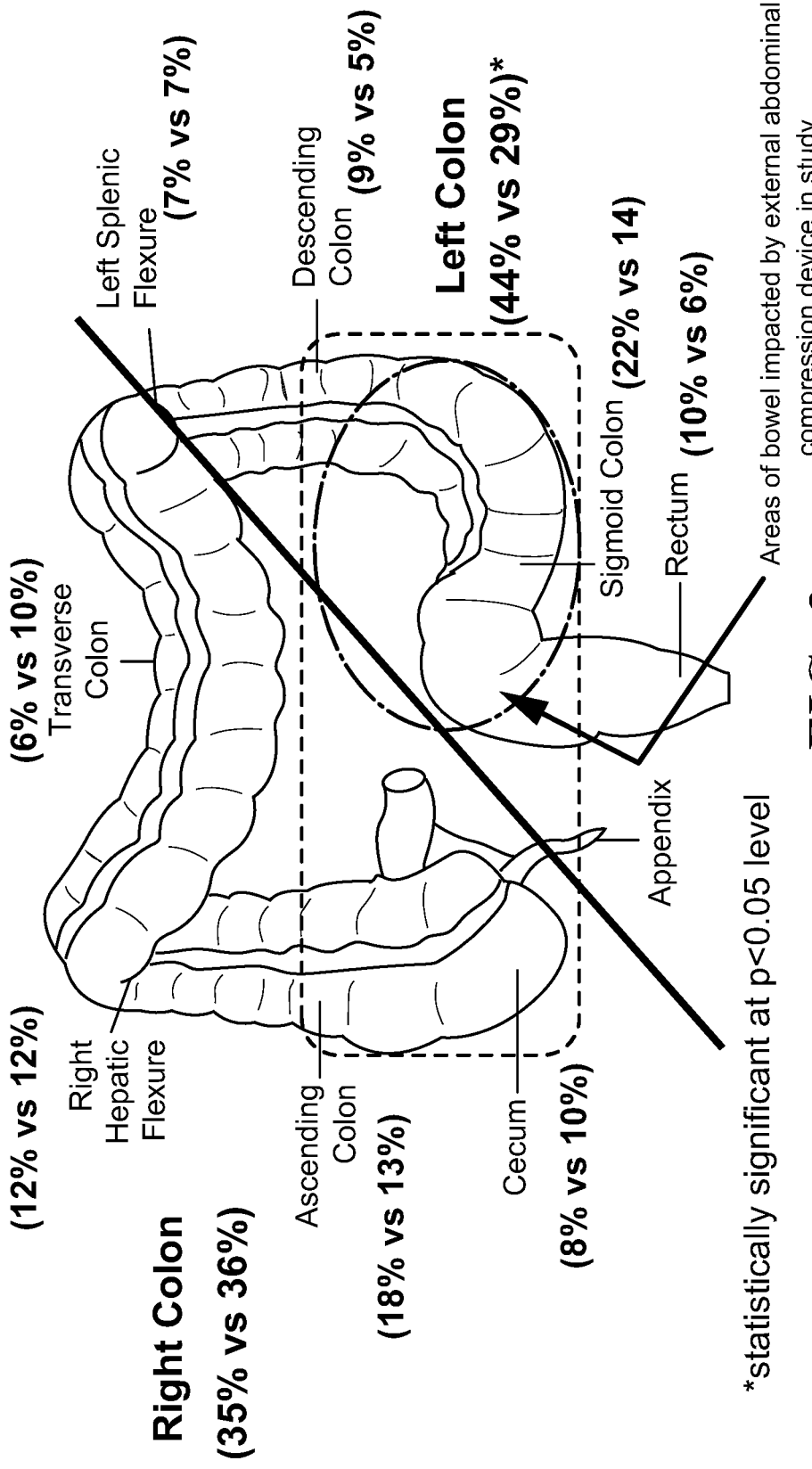
FIG. 3 illustrates aspects of FIG. 1 and FIG. 2 layered on top of each other.

FIG. 3 layers FIGS. 1 and 2 on top of each other to demonstrate that i) improvements in adenoma detection (treatment over the sham group) are observed in regions of the colon impacted by the application of compression during withdrawal of an endoscopy, and; ii) that the most significant ADR improvement (22% vs 14%) occurs in the region of the colon (sigmoid) where additional, focused compression (relative to other regions that are only receiving 'baseline' compression) is provided.

Figure 4:
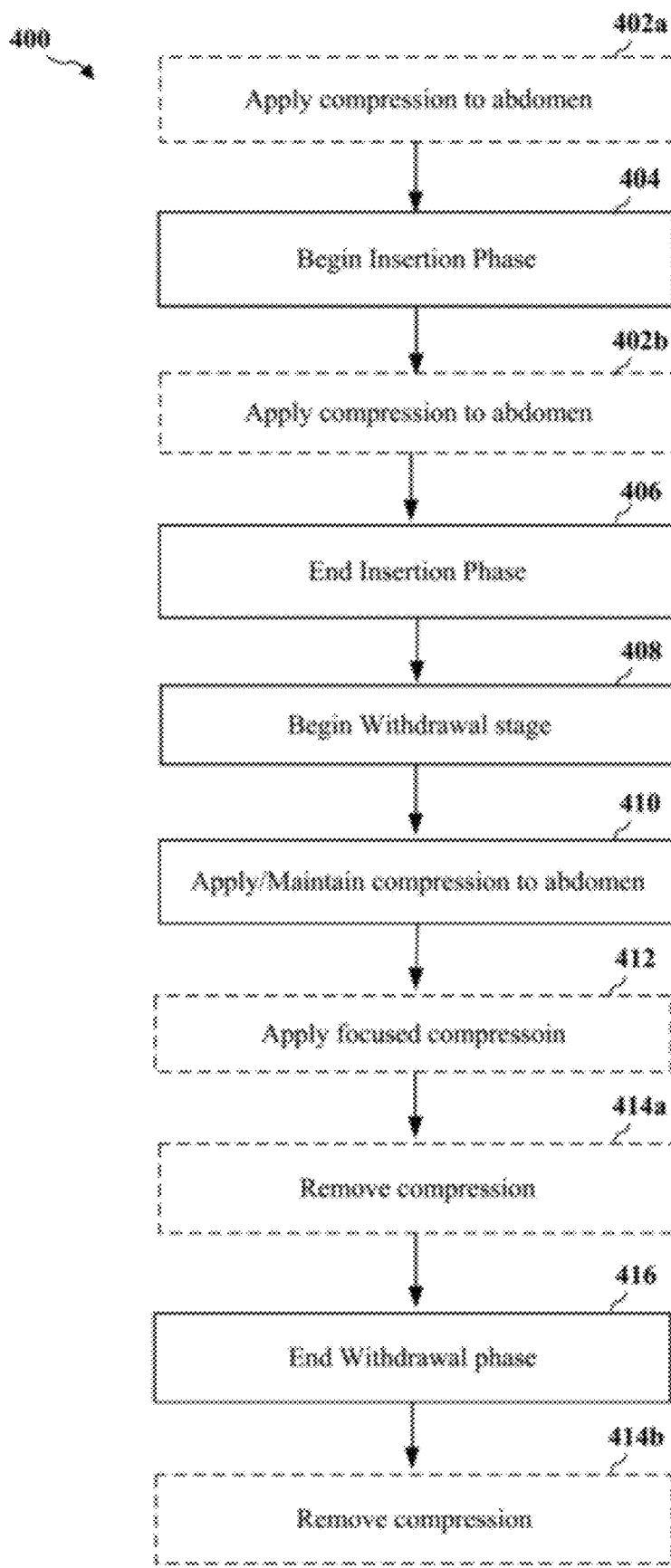
FIG. 4 illustrates showing aspects of a method for improving adenoma detection during an endoscopy procedure.

FIG. 4 illustrates a flow chart 400 showing aspects of a method for improving adenoma detection during an endoscopy procedure. At 402, the method may include applying compression to the abdomen of a patient prior to beginning an insertion phase at 404. As an alternative, the compression may be applied to the abdomen at 402b after the insertion phase begins. The compression may be applied, e.g., in an area extending approximately from the pubic region to the top of the abdominal region. Thus, the compression may be applied at a location beginning at approximately just above the genitals and ending at approximately just below the ribcage. In another example, compression may be applied to a smaller region extending only partially between the pubic region and the top of the abdominal region, e.g., the suprapubic area extending from approximately just above the pubic bone to the umbilicus, the left lower abdomen bounded approximately by the umbilical line, the midline, and the crest of the left hip, the left upper abdomen bounded approximately by the umbilical line, the midline, and the lower left ribcage, the right lower abdomen bounded approximately by the umbilical line, the midline, and the crest of the right hip, and the right upper abdomen bounded approximately by the midline, the umbilical line, and the lower right ribcage.

At 406, the insertion phase ends, and a withdrawal phase of the endoscopy procedure begins at 408. The withdrawal phase may begin, e.g., when the operator begins to withdraw or remove the endoscope from the patient.

At 410, compression of the patient's abdomen is maintained during withdrawal of an endoscope. The compression may be maintained throughout the withdrawal phase of the endoscopy procedure. After the withdrawal phase of the procedure is finished, the compression may be removed at 414b. The compression may be removed at 414a, prior to the end of the withdrawal phase. Compression may also be initiated or applied at any point during the withdrawal of the endoscope, e.g., as illustrated at 410.

Thus, the compression may be applied to the abdomen prior to insertion of the endoscope. In another example, illustrated at 402a, the compression may be applied after the insertion phase has started at 402b. Thus, the compression may be applied and maintained throughout both the insertion and withdrawal phases of the endoscopy procedure, or the compression may be maintained only for a portion of the withdrawal phase, e.g., being applied at 410 and removed at 414a. Prior to use of the compression during the withdrawal phase, the compression may also be applied and removed at certain stages of the insertion phase, e.g., at 402a and being removed prior to reapplication at 410. Thus, iterative/intermittent compression may be applied. The compression may be temporarily applied to a particular region of the colon, e.g., as illustrated at 412. This focused compression may be removed prior to removal of the compression to the abdomen. Then, focused compression may be temporarily applied to another region of the colon. Additionally, compression may be reapplied to the same portion of the colon. This may be used to improve visualization of the portion of the colon, or may be used to adjust or change the visualization of that region of the colon. Optional aspects in the flow chart 400 are illustrated using a dashed line.

Compression may be applied to the abdomen of the patient using various compression devices. One example of a compression device that may be used to apply constant pressure to the abdomen of the patient during withdrawal of an endoscope is an elongated elastic band that is wrapped around the abdomen of the patient and secured. For example, compression may be applied by wrapping a band of elastic material around the abdomen of a patient. Then, one end of the band may be connected or fastened to another portion of the band to maintain tension in the band in order to apply constant compression to the abdomen of the patient.

Aspects may further include, prior to connecting the one end of the band to the another portion of the band, tensioning the band to apply a desired degree of pressure to the patient's abdomen through contraction of the band across at least a portion of the patient's abdomen once it is applied.

Aspects of an example elastic band are detailed in U.S. application Ser. No. 13/344,715, titled "Method and Apparatus for Tensile Colonoscopy Compression" filed on Jan. 6, 2012, and published as U.S. Publication No. 2013/0178893 A1, U.S. application Ser. No. 14/575,860, titled "Endoscopy Band with Sigmoid Support Apparatus" filed on Dec. 18, 2014, and published as Publication No. 2015/0105699; Provisional Application No. 61/917,469, titled "Colonoscopy Band with Sigmoid Splint" filed on Dec. 18, 2013 and Provisional Application No. 61/944,658 titled "Endoscopy Band with Sigmoid Support Apparatus" filed on Feb. 26, 2014; the entire contents of each of which are incorporated herein by reference.

For example, FIGS. 5-8 illustrate an example device 8 for applying compression to the abdomen during withdrawal of an endoscope. The device 8 illustrated in FIG. 5 includes a primary elongated band or wrap 10 of sufficient length for placement around a patient's lower abdomen. A closing mechanism 12 may be provided at the end of the primary band to secure the device around the patient so that it provides the desired amount of broad support and compression. A handle 14 may be sewn onto the exterior of one or both ends of the primary wrap to assist in fastening and closure. Aspects may include, an insert 16 attached to the primary wrap 10 or used in conjunction with the primary wrap 10 to provide directed force to the sigmoid colon.

The primary wrap 10 preferably has a circumferential length between approximately 15 and 75 inches in order to accommodate varying abdominal girths in patients. The preferred width of the primary wrap 10 is between 6 and 10 inches, although variations having widths of between 3 and 20 inches may be used depending on the size of the patient and to accommodate special circumstances such as an abdominal hernia or a large pannus. For example, the primary wrap may be configured to have a width that allows it to be fastened around the patient's lower abdomen with the upper edge of the wrap just below the umbilicus and the bottom edge of the wrap along or close to the pubic line. The width of the primary wrap may be selected so as not to be so large that the upper edge conceals the umbilicus and additional areas of the abdomen above the umbilicus. This configuration may be made in order to avoid pressure on the diaphragm or stomach, as pressure on the diaphragm and stomach during colonoscopy can increase the risk of oxygen deprivation and aspiration events, respectively, due to the fact that the patient is generally sedated during the procedure. At times, certain patients may benefit from a slightly higher placement, e.g., having the device slightly above the umbilicus, yet below the rib cage. It is still important to avoid putting pressure on the diaphragm and/or stomach of a sedated patient. The primary wrap 10 may comprise, entirely or in part, a flexible, bio-compatible foam, rubber, neoprene, polyester, nylon, non-woven or woven fabric, mesh fabric, synthetic fabric, microfiber fabric, silicon or vinyl plastic, or any other materials generally known to be used in medical fabrics and goods. The primary wrap 10 may be composed of both elastic and inelastic materials.

Figure 5:
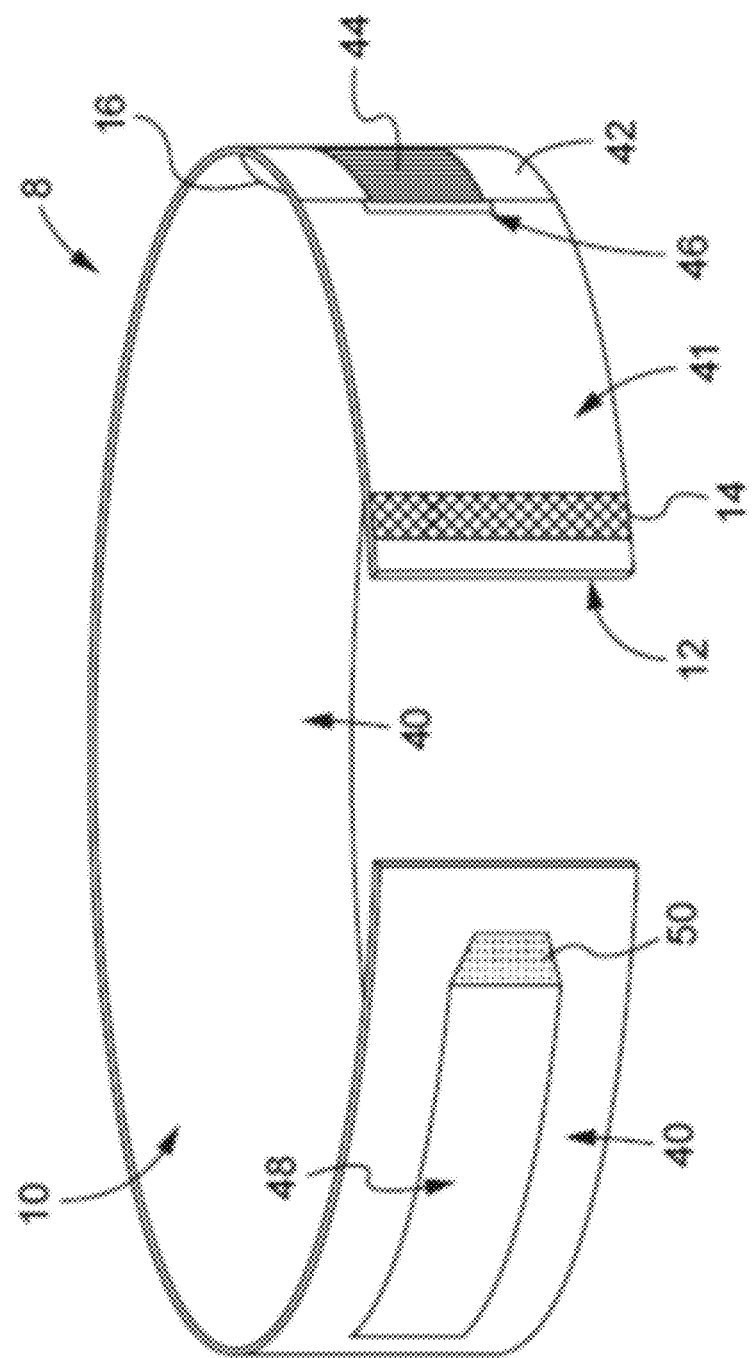
FIGS. 5, 6, 7, and 8 illustrate aspects of example compression devices in accordance with aspects presented herein.

A primary abdominal band may comprise two or more sections that vary in material type. In one example, as depicted in FIG. 5, two sections—one larger 40, and one smaller 41—of the primary abdominal band 10 may be composed of a flexible, elastic or semi-elastic, medium-thickness, latex-free neoprene with thin polyester or nylon glued to its interior and exterior sides. Among others, this material may be capable of providing broad, firm, yet comfortable support to the patient's abdominal region. A third section 42 of the primary wrap 10 may comprise a relatively inelastic material, such as a woven fabric. The inelastic section 42 may be provided at the location into which or under which the insert is placed. Upon deployment of the device, the inelastic section 42 may be positioned in the patient's lower left abdominal quadrant, over the sigmoid region.

For the primary wrap to provide appropriate general compression and support, it may be important that the wrap remain flat against the body when fastened around the abdomen. This is notable because certain materials and designs have a tendency to roll-up when stretched or wrapped around the abdomen, particularly when the device is being applied to patients with a large pannus. To prevent roll-up from occurring, aspects of the invention may include reinforcements to ensure that the primary abdominal wrap remains flat against the body when used in patients of varying body sizes. This may be accomplished by the application of serge stitching along the edges of the primary abdominal band.

In other examples, compression may be applied to the abdomen using devices that do not involve an elastic band. For example, such devices might include Inelastic materials wrapped about the abdomen, textiles and apparel designed to exert abdominal compression when worn about the abdomen, apparatuses that incorporate pneumatic mechanisms such as inflatable air bladders to apply compression to the abdomen, items that apply pressure to the abdomen using the patient's body weight and gravity such as shaped items designed specifically for colonoscopy that are placed between the patient's body and the operating table so that the patient's body weight compresses the shaped item into the abdomen; apparatuses such as firm, shaped foam items that are manually compressed into the abdomen by a nurse or technician; weighted materials and apparatuses such as a weighted blanket laid across the abdomen that applies compression as a result of gravity; mechanisms that exert force about or across the abdomen through mechanical leverage such as elastic or inelastic materials with a lace or crank closing mechanism that pulls two ends of the material together around an abdomen or portion thereof to exert compressive force, or a hinge mechanism that pulls and stretches a material across the abdomen after it has passed through a hinge in order to exert compression; robotic systems with appendages and apparatuses for applying external compression; tools, mechanisms, and pharmacological preparations that provoke or promote contraction of the musculature of the abdomen and surrounding ligature which has the effect of exerting compressive force upon the colon; and compression that is applied manually by hand by a staff member, or manually by a device that the staff member/user compresses against or into the abdomen.

Figure 12:
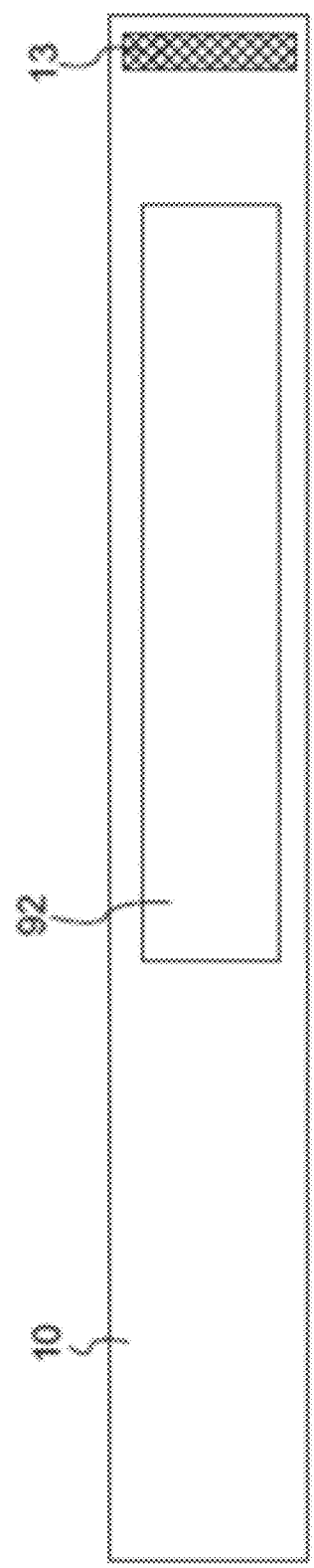

As depicted in FIGS. 4-7, a short strap 44 may be attached along its own right vertical edge to the right vertical edge of the inelastic section 42. The strap 44 may lay to the left, and extends just past the left vertical edge of the inelastic section 42. On the end of the strap 44 not attached to the inelastic section 42, there may be a small hinge 46. There may also be another, longer strap 48 attached along the larger neoprene section 40 of the exterior primary wrap 10. The longer strap 48 may be positioned approximately midway along section 40. Once the primary wrap has been fastened by its closing mechanism 12, this strap 48 may be passed across the closing mechanism 12 of the primary wrap 10, through the hinge 46 on the short strap 44, and then doubled-back and pulled toward the direction from which it came. At the unattached end of the long strap 48, there may be a patch of VELCRO® or hook material 50 (visible in FIG. 4, 6), and on the opposite of the side of this end of the long strap 48, a small handle 52 (visible in FIGS. 5, 7.) Once the strap 48 passes through the hinge 46, this strap may be tightened and fastened by the nurse or assistant to exert additional, directed force to the sigmoid colon through the insert 16. As depicted in FIG. 12, this aspect may allow nurses and technicians to easily adjust the force on the sigmoid colon from the location in the procedure or operating room in which they are most often positioned during a colonoscopy, It additionally eliminates the need for the nurse or assistant to provide manual abdominal compression, thereby reducing their risk of musculoskeletal injury. Additionally, this example allows for the device to be quickly and easily removed should the need arise.

Thus, as illustrated in FIG. 12, the strap is coupled, e.g., sewn, to a portion of the wrap that is configured for placement over a left side of the patient's lower abdomen. The strap is pulled from left to right, e.g., pulled across lower abdomen and left lower abdominal quadrant from left side of body towards right side of body. This can be helpful because the patient typically lies on their left side during the procedure. Because the strap pulls from left to right across the lower abdomen, additional leverage and compression may be generated by the patient's body when the strap is in place. As the strap goes from left to right also allows the level of compression generated by the device to be easily adjusted during the procedure, e.g., while the patient is lying on their left side.

Thus, the strap is connected to the wrap in a manner that it extends under the patient during a procedure. The strap can then be pulled opposite the portion under the patient in order to use the weight of the patient's body to adjust the compression applied by the strap.

As illustrated in FIG. 4, the method may further include applying focused compression to at least a portion of the abdomen of the patient at 412. Although this is illustrated as a separate aspect, applying focused compression may be accomplished at the same time as applying compression to the abdomen. For example, focused compression may be applied to a left lower abdomen of the patient. Focused compression may be applied in an area directed to a left colon region and sigmoid colon of the patient. Focused compression may also be applied to a left upper abdomen, a right lower abdomen, a right upper abdomen, a right colon region, a cecum, an ascending colon, a hepatic flexure, a transverse colon, a splenic flexure, a descending colon, and a rectum. As another example, focused compression may be applied to a particular region of the abdomen without applying general compression to the abdomen. For example, specific compression may be applied to the transverse colon without applying a substantial amount of general compression to the abdomen. Thus, the compression indicated at 404 may be a focused compression or may be a general compression applied across the abdomen.

Figure 7:
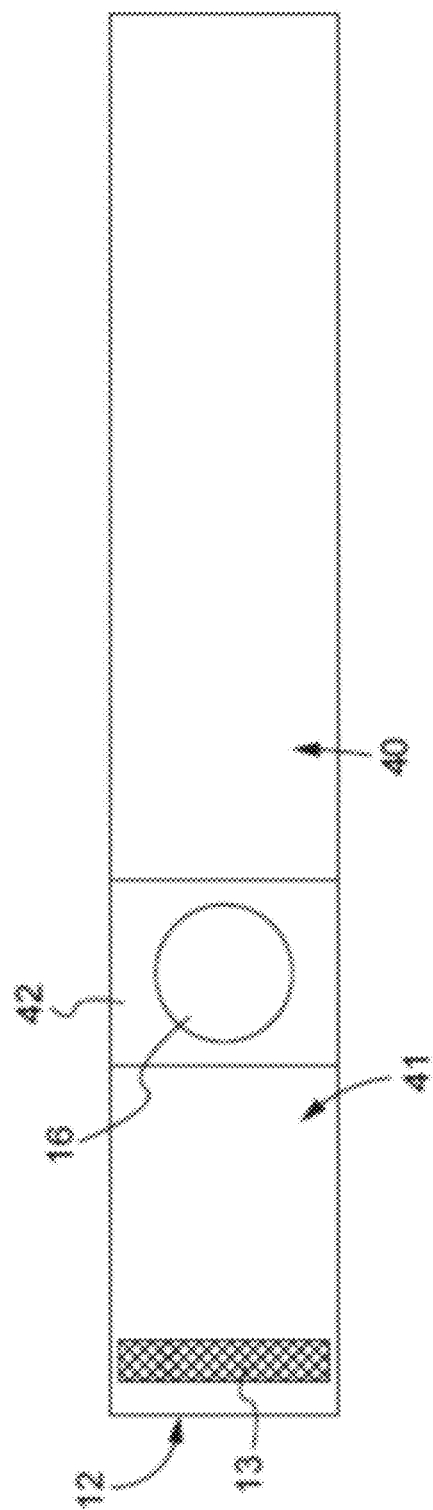
Figure 8:
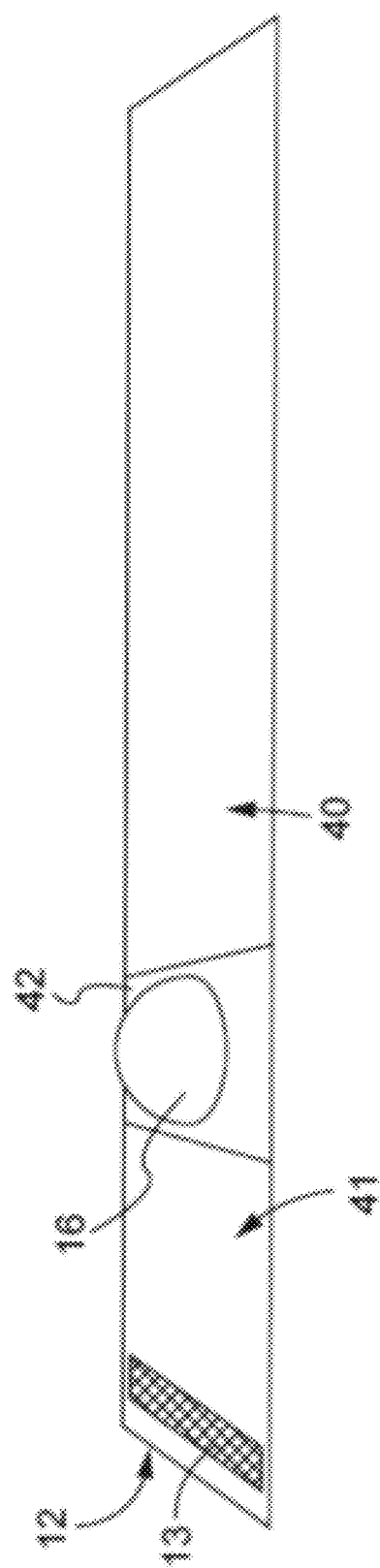

Among other mechanisms, adjustable, focused pressure may be applied to a particular region of the patient's abdomen using an insert. Thus, a compression device may also accommodate an insert or attachment that provides specific support to the sigmoid colon. FIGS. 5, 7, and 8 illustrate one example of an insert 16.

Figure 6:
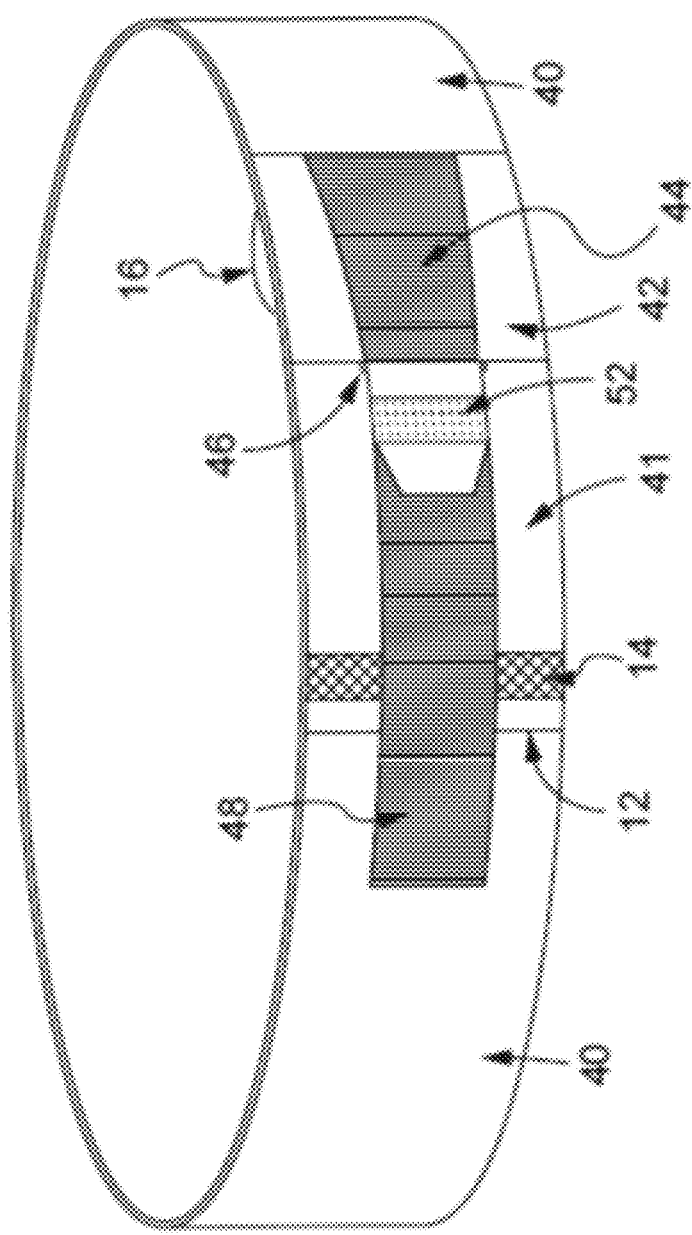

FIG. 10 illustrates an example tapered insert 1102, placed in a vertical orientation, alongside an example of a non-tapered insert 1104 in order to illustrate the potential for the non-tapered insert to pinch the colon and hinder the advancement of the scope. In another example, the shape of the insert may resemble a semi-hemisphere, with the flat side of the insert placed against the wrap and the circular side of the insert held against and pressed into the patient's sigmoid colon. An example of a semi-hemisphere insert 16 is illustrated in FIGS. 6-8.

The insert may be held against the patient's body by a nurse or assistant, and then the primary wrap be fastened around the patient's abdomen and overtop of the insert. This causes the insert to be positioned between the patient's abdomen and the wrap. The wrap helps to maintain the insert at the desired placement and applies pressure to the insert. Alternately, the insert may be attached to the device by an adhesive, Velcro, or magnets while the primary wrap is fastened. In one aspect, there may be a pouch sewn or otherwise attached to the primary wrap into which the insert may be placed. The insert may also be embedded in the wrap. Such a pouch may be accessible on the interior, exterior, or both sides of the primary wrap, providing the user the option to add the insert to the primary wrap when deemed necessary. In an alternative embodiment, the insert may be sewn or attached into or onto the primary wrap during manufacturing and in this case may be a non-removable, inherent product feature. In other aspects, the actual insert may be incorporated into the primary wrap during manufacturing, and certain appendages may emerge or extend from the insert or the pouch in which the insert is placed. These appendages may be used, e.g., to facilitate the measurement of the force generated by the insert upon the patient's abdomen, the monitoring of vital signs, or the capture of other data relevant to the patient's health and safety.

The insert may comprise materials that, when pushed, pulled, or otherwise pressed against the patient's abdomen, are able to provide moderate to firm direct force to the sigmoid colon, without causing discomfort or pain for the patient or impeding the colonoscopy procedure in any way. In one example, the insert may comprise a firm foam material. In another example, the insert may comprise a semi-flexible plastic, in a third, a semi-flexible silicone composite, and in a fourth, an inflatable plastic or composite air bladder. The insert may additionally comprise paper, rubber, neoprene, or fabric, or a combination of any of these materials or those listed in the previous sentence, and also in conjunction with a hard object around which these materials are wrapped. An important aspect of the composition of the insert may be that, when it is compressed into the abdomen, it should be firm enough to facilitate the passage of the scope, but flexible enough that in providing compression, it does not hinder the passage of the scope instead.

Figure 9:
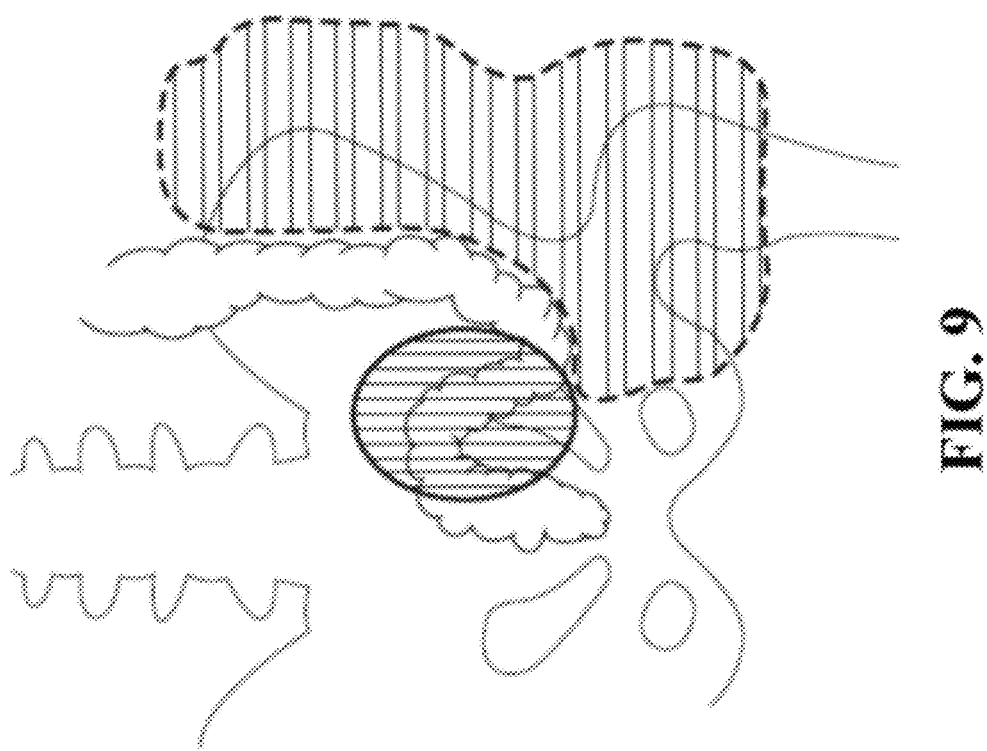
FIG. 9 illustrates example areas of focused compression in accordance with aspects presented herein.

Another important element of the insert may be its size. While the insert used in the invention may vary to accommodate differing body types and sizes, any insert used to provide localized compression to the sigmoid colon region may be of a size that, when positioned over the sigmoid colon, is capable of being compressed into the left lower quadrant of the abdomen generally, and the sigmoid colon specifically, without it being impeded by any other anatomical feature. Relevant anatomical features that may be accounted for include the left pelvis and hip. FIG. 9 depicts an example target area on the body for compression, with the hashed-area in the drawing indicating the anatomical features that might impede the insert in compressing the sigmoid colon if the size of the insert is too large.

Another important aspect of the insert may be the shape of the insert. The insert shape may be configured to provide firm pressure to the sigmoid colon without pinching the colon or compressing the lumen in a way that impedes the movement of the endoscope. Aspects presented herein address this concern by tapering the edges of the insert to reduce the likelihood of the insert pinching or closing of the colon when compressed by the device. In one embodiment, the shape of the insert may approximately resemble the shape of a small souvenir football. When deployed, this insert may be placed in either a horizontal or vertical orientation. FIG. 10 illustrates an example tapered insert 1002, placed in a vertical orientation, alongside an example of a non-tapered insert 1004 in order to illustrate the potential for the non-tapered insert to pinch the colon and hinder the movement of the scope. In another example, the shape of the insert may resemble a semi-hemisphere, with the flat side of the insert placed against the wrap and the circular side of the insert held against and pressed into the patient's sigmoid colon. An example of a semi-hemisphere insert 16 is illustrated in FIGS. 7 and 8.

Although, the insert may offer additional functionality beyond applying force to the sigmoid colon. Through testing, a standard may be developed that identifies and recommends the optimal amount or range of force needed to optimally support the colon in various patient groups. Accordingly, having some type of force measurement system built into the insert may be a natural way to provide device operators with knowledge regarding the amount of force they are exerting on the patient's sigmoid colon. Having such knowledge could improve the safety, consistency, and effectiveness of the device and the application of pressure during a colonoscopy generally.

Figure 11:
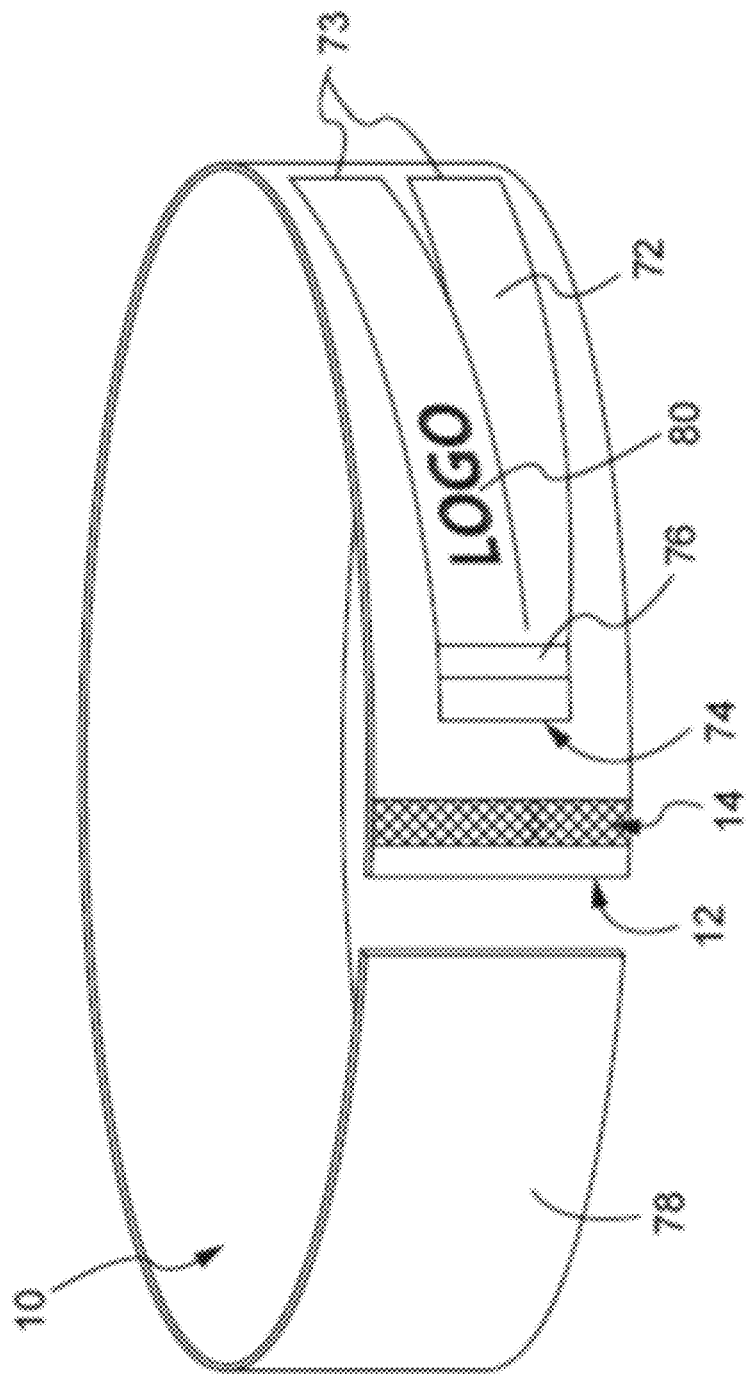
FIGS. 11, 12, 13, 14, 15, and 16 aspects of example compression devices in accordance with aspects presented herein.

Another example of a mechanism for applying focused compression to a specific area of the abdomen and colon is a compression device as depicted in FIGS. 11 and 12 illustrate an example compression device that may include a primary wrap 10, with a closing mechanism 12, and a handle 14 to assist in fastening the primary wrap around the patient's lower abdomen and a secondary strap 72 for applying additional, focused compression to a specific location—in this case the sigmoid colon. The device may also include one or more secondary straps designed and positioned to apply focused compression to any one or more of the left lower abdomen, left upper abdomen, right lower abdomen, right upper abdomen, right colon, left colon, cecum, ascending colon, hepatic flexure, transverse colon, splenic flexure, descending colon, sigmoid colon and rectum. The device may also include a secondary strap 72 attached to the exterior side 78 of the primary wrap 10, with a closing mechanism 74 that allows the strap, e.g., to be fastened to the exterior side 78 of the primary wrap 10. In an aspect, the closing mechanism 74 of the secondary strap 72 may comprise a hook strip 75 on the inside of the secondary strap 72 that is capable of fastening anywhere along the exterior side 78 of the primary wrap 10—the hook strip 75 on the secondary strap 72 is visible in FIG. 21. In this example, the exterior side 78 of the primary wrap 10 comprises a hook-compatible material to which the hook strip 75 can be fastened and remain fastened while the secondary strap is stretched and under tension. The secondary strap 72 is constructed of an elastic or semi-elastic material that is capable of retaining tension when stretched horizontally and fastened to the exterior side 78 of the primary wrap 10 using the closing mechanism 74. The secondary strap 72 may comprise the same or different materials than the materials comprised in the primary wrap 10. The secondary strap 72 may comprise one or more layers of materials. In an example, the secondary strap 72 may comprise an elastic strap the entire length of which equals approximately twice the intended length of the secondary strap 72. In this example, the elastic strap may be doubled-over, and both ends may be sewn to the exterior 78 of the primary wrap 10 along the same vertical line 73, creating the horizontal 'V' appearance of the secondary strap 72 shown in FIG. 11. Doubling-over the material composing the secondary strap can serve to increase the breadth and force generated by the secondary strap, while preventing the incurrence of additional materials costs that would be associated with using a taller, single-layered strap instead. The midpoint of the secondary strap may be positioned approximately over the patient's lower left quadrant once it is stretched and fastened.

An insert may or may not be used with a secondary strap. Should an insert be used with this embodiment, the insert may be positioned against the exterior side 78 of the primary wrap 10, in the preferred anatomical location. Once properly positioned, the secondary strap 72 may then be passed over the top of the insert, stretched to tension, and fastened using the closing mechanism 74. The force exerted upon the insert by the tensioning of secondary strap 72 may serve to press the insert into the body. Mechanisms for indicating stretch and compression, such as those described in Publication No. 2015/0105699.

Aspects presented herein may also help the patient feel warm and comfortable. In FIG. 12, e.g., a primary wrap 10 may be equipped with a pouch 92 that is attached or fastened to the interior side of the primary wrap 10. This pouch 92 may be capable of accepting and holding in place re-usable or disposable heating apparatuses, including the rectangular heating pad 94 shown in FIG. 19.

Figure 13:
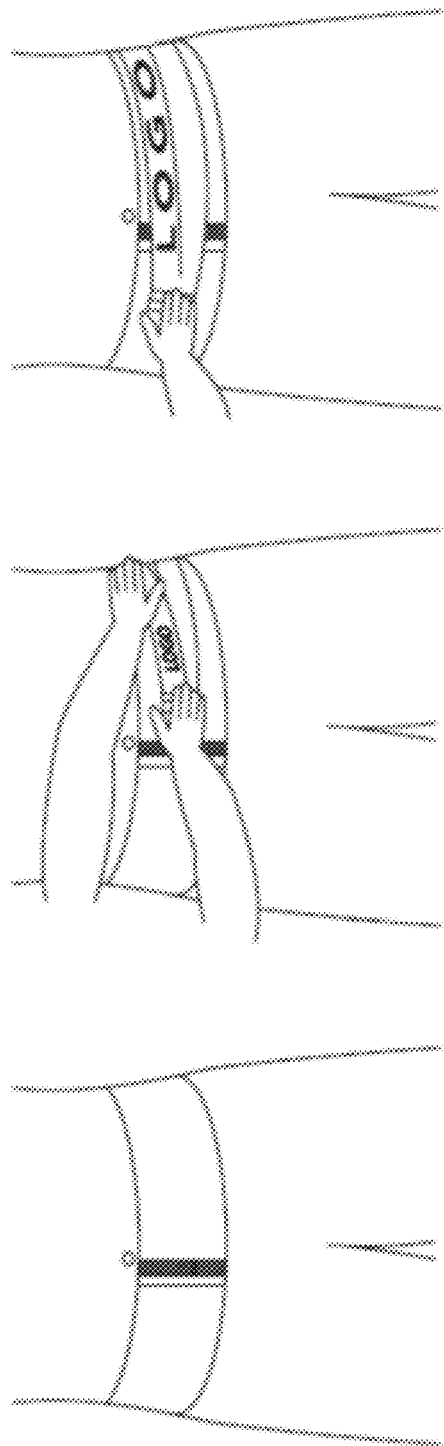
Figure 14:
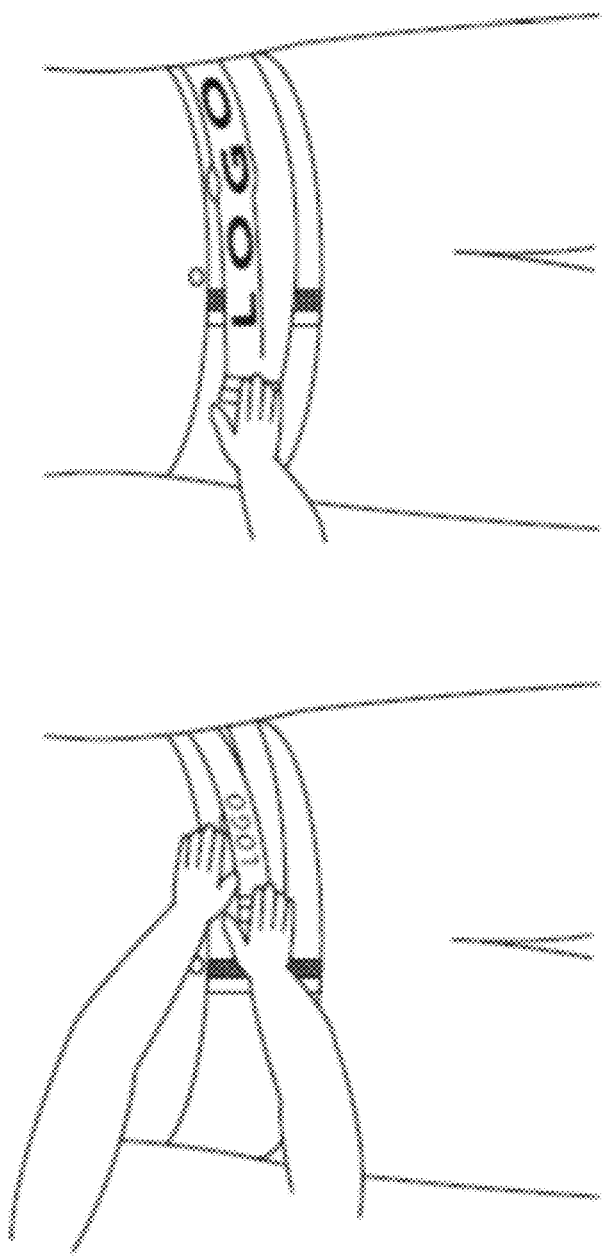
Figure 15:
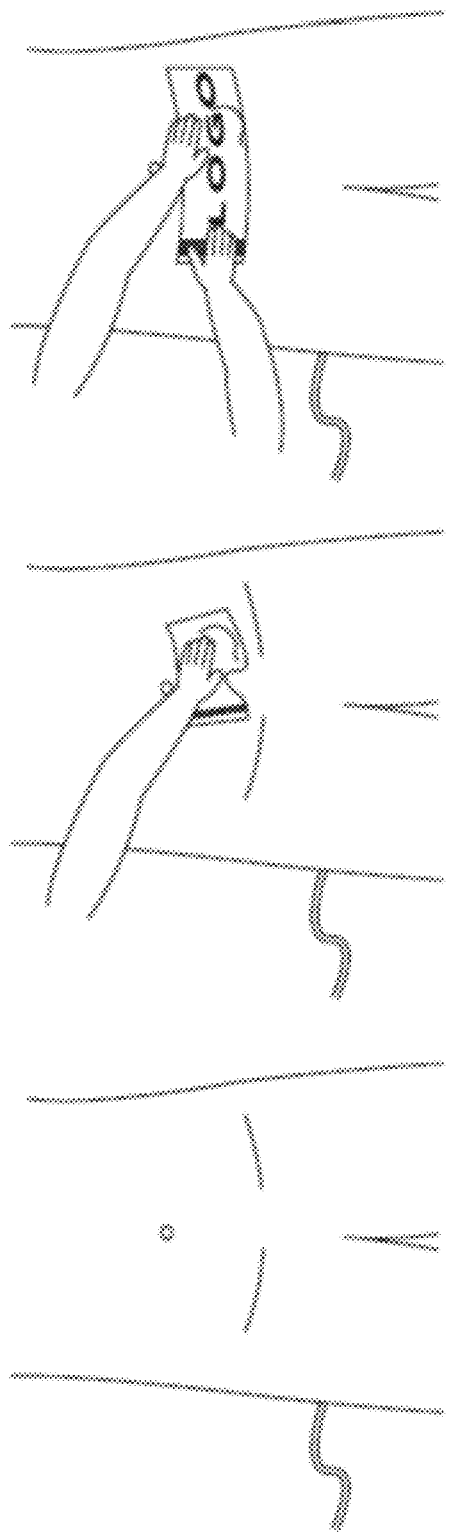
Figure 16:
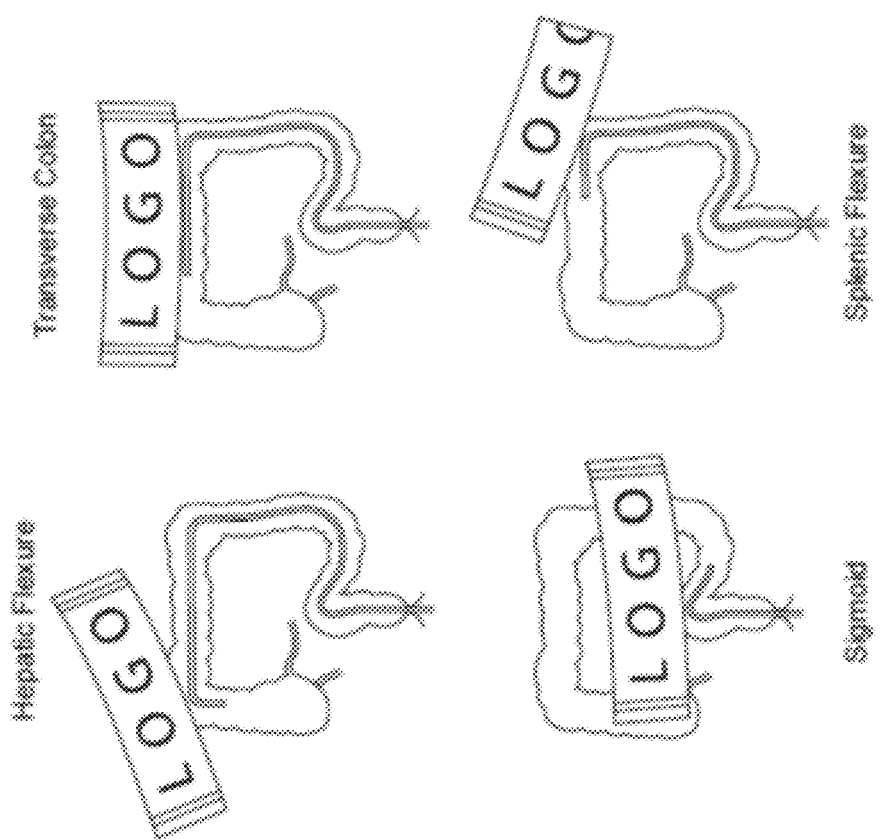

Other aspects may also incorporate a different type of secondary strap to exert additional, location specific force is depicted in FIGS. 13 and 14. Unlike the aspect depicted in FIG. 11 where one vertical side of the secondary strap is affixed to the device, the secondary strap in the aspect shown by FIGS. 13 and 14 may be fully detachable from the primary wrap, and may have fastening mechanisms at both ends that allow the strap to be secured the exterior side of the primary wrap. The secondary strap in this aspect may be either re-usable or disposable, and may be capable of being stretched and maintaining tension, or may use another mechanism to exert compressive force, when it is secured to the primary band. An insert may be used with the detachable secondary strap, as demonstrated in FIG. 14. FIG. 15 depicts an example that includes only one strap. The strap in this example might not wrap fully around the patient but instead may be stretched directly about the location on the patient's body where force is desired. The strap may be equipped with fastening mechanisms on each end, e.g., to allow the strap to adhere directly to the patient's body. Such a wrap may be used with an insert. The insert may be separate from the strap, or may be affixed to or build into the strap. The strap and insert in this embodiment may be either re-usable or disposable. Such aspects might be particularly helpful in instances when unexpected looping occurs, particularly in areas of the bowel less prone to looping. FIG. 16 illustrates schematically how the wrap may be used to address looping at the splenic flexure, in the transverse colon, or at the hepatic flexure.

In another option, the amount of force being applied by the endoscopy sigmoid support apparatus may be measured using a compression indicator, as illustrated in FIG. 13-15. Among others, the indicator may comprise a gauge for measuring and indicating the amount of pressure applied to the abdomen of the subject and/or a visual indicator. For example, a strip of material may be used having at least one transparent window through which a mark or a set of marks can be viewed in order to determine the amount of pressure being applied. In another example, a visual mark may be provided directly on an elastic portion of the apparatus, and the deformation of the visual mark may be used to determine an amount of pressure being applied. An example deformed mark may be provided so that an operator can compare the example deformed mark to the deformation of the visual mark.

In addition to an insert and a secondary strap other aspects may be used to apply focused, adjustable compression to a particular area of the abdomen including: one or more pneumatic mechanisms such as air bladders positioned at one or more specific regions of the abdomen and colon, items that apply pressure to a specific portion of the abdomen or colon using the patient's body weight and gravity such as shaped items designed specifically for colonoscopy that are placed between the patient's body and the operating table so that the patient's body weight compresses the shaped item into a particular location or region of the abdomen; apparatuses such as firm, shaped foam items that are manually compressed into a specific region of the abdomen or colon by a nurse or technician; weighted materials and apparatuses such as a weighted ball or sandbag laid upon a specific portion of an abdomen or colon that applies compression as a result of gravity; mechanisms that exert force about or across a specific region of the abdomen or colon through mechanical leverage such as elastic or inelastic materials with a lace or crank closing mechanism that pulls two ends of the material together around, across, or about a specific region of an abdomen or colon in order to exert compressive force, or a hinge mechanism that pulls and stretches a material around, across, or about a specific region of an abdomen or colon after it has passed through a hinge in order to exert compression; a robotic system with appendages and apparatuses for applying external compression to specific regions of the abdomen or colon; tools, mechanisms, and pharmacological preparations that provoke or promote contraction of the musculature of a specific region of the abdomen and surrounding ligature which has the effect of exerting compressive force upon a specific, localized region of the colon; responsive technology equipped with endoscope proximity sensors that automatically applies focused compression to specific areas of the abdomen, based on location of the endoscope and other factors, using any of the mechanisms described herein for applying abdominal compression and any others commonly known in the art, and compression that is applied manually by hand by a staff member, or manually by a device that the staff member/user compresses against or into the abdomen.

An external, abdominal compression device was recently evaluated in a trial of patients undergoing colonoscopy. Patients in the study were randomized to one of two groups, the treatment group and the sham (control) group. Patients randomized to the treatment group underwent colonoscopy with an external abdominal compression device fastened around their abdomen. The device provided general, broad lower abdominal support and additional, focused pressure to the left lower abdomen and sigmoid colon region. The device was applied just prior to the procedure and remained engaged during the insertion and withdrawal phases. Patients randomized to the sham group underwent colonoscopy with a non-functional, disengaged wrap around their abdomen that exerted no pressure whatsoever. The sham device was used as a means to blind (prevent) physicians participating in study from knowing whether a patient did or did not have the abdominal compression device engaged for their procedure.

The primary measure of adenoma detection is adenoma detection rate (ADR). ADR describes the number of patients in whom one or more adenomas are detected as a percentage of total colonoscopies performed. Current gastroenterology guidelines stipulate that competent physicians performing colonoscopy should achieve an ADR of 15% in women and 25% in men.

Use of the external abdominal compression device provides an unexpected enhanced adenoma detection rate of approximately 43% relative to the control group 40%. Sub-population usage may provide even more dramatic improvements in ADR associated with use of the compression device, e.g., among women (40% vs 30%), patients 60 and older (53% vs 39%), and patients with a BMI>30 (53% vs 40%).

For example, a per-protocol analysis yields similar conclusions with respect to the impact of the abdominal compression device on ADR:
  Overall enhancement of adenoma detection (43% ADR in treatment group vs 40% in sham group);
  Female patients (40% vs 30%);
  Patients 60 and older (51% vs 40%);
  Patients with BMI>30 (52% vs 40%).

The use of external abdominal compression to facilitate insertion and advancement of an endoscope into and through the bowel can be very important. The basis for the application of abdominal pressure during insertion is to support and provide counter-pressure to the colon to reduce the formation of loops that hinder the advancement of the scope to the cecum. This need is obviated, however, during the withdrawal phase as loops are naturally reduced by the motion of the scope being withdrawn from the body.

As the reason for applying abdominal pressure during insertion was absent in the withdrawal phase, there has been no reason to apply compression during withdrawal. As presented herein, unexpected, enhanced ADR may be achieved through the use of compression during a withdrawal phase of an endoscopy.

Analysis of the location of detected adenomas yielded additional unexpected, yet compelling findings supporting the benefit of abdominal compression during withdrawal. This analysis was performed on a per-protocol basis in order to exclude patients in the intervention group for whom the device was not properly engaged during the withdrawal phase of their procedure. For the purposes of this analysis, adenomas were classified into one of eight colon sections corresponding with the region in the colon where the adenoma was detected. These eight sections included: the cecum, ascending colon, hepatic flexure, and transverse colon, collectively making up the Right colon; and the splenic flexure, descending colon, sigmoid colon, and rectum, collectively making up the Left colon.

FIG. 2 and FIG. 3, demonstrate that adenoma detection rate (ADR) may be improved in several specific regions of the colon in patients who received the abdominal compression device:
  Ascending colon (18% vs. 13%);
  Descending colon (9% vs 5%);
  Sigmoid colon (22% vs 14%), and,
  Rectum (10% vs 6%).

What is very clear is that each of the regions of the colon in which an improvement may be provided with the compression device are regions that are within the example device's zone of compression (e.g. were compressed by the device). As further evidence of the unexpected finding that abdominal compression during withdrawal improves adenoma detection, it is important to note the region of the colon in which the largest improvement in adenoma detection associated with the use of the compression device occurred: the sigmoid colon. As depicted in FIG. 1 and FIG. 3, the sigmoid colon is the area upon which the example abdominal compression device provided additional, focused pressure.

Example aspects of the present invention have now been described in accordance with the above advantages. It will be appreciated that these examples are merely illustrative of aspects of the present invention. Many variations and modifications will be apparent to those skilled in the art.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more."

The invention claimed is:

1. A method for improving adenoma detection, comprising:
   applying compression to the abdomen of a patient, wherein the compression of the abdomen is provided via elastic contraction provided by a wrapping an elongated band of elastic material around the abdomen of the patient and connecting one end of the elongated band to another portion of the elongated band to maintain tension in the elongated band, wherein consistent pressure to and across the abdomen of the patient is provided to the patient's abdomen across a surface of the elastic band that extends across the abdomen of the patient in order to reduce loops in the patient's colon and facilitate passage of an endoscope; and
   maintaining the compression of the abdomen of the patient during withdrawal of the endoscope while examining the lining of the colon.

2. The method of claim 1, further comprising:
   tensioning the band prior to connecting the one end of the band to the another portion of the band to apply a desired degree of pressure to the patient's abdomen through contraction of the band across at least a portion of the patient's abdomen.

3. The method of claim 1, wherein the compression is applied to the abdomen of the patient prior to and during an insertion and advancement of an endoscope.

4. The method of claim 1, wherein compression is maintained throughout a withdrawal phase of an endoscopy procedure.

5. The method of claim 1, wherein compression is applied at a location beginning at approximately the hips of the patient and ending at approximately the umbilicus of the patient.

6. The method of claim 1, wherein compression is applied at a location beginning approximately at the hips of the patient and ending at approximately just below the patient's rib cage.

7. The method of claim 1, further comprising:
   applying focused compression to at least one selected from a group consisting of:
   a left lower abdomen of the patient,
   a left upper abdomen of the patient,
   a right lower abdomen of the patient,
   a right upper abdomen of the patient,
   a cecum region of the patient,
   an ascending colon region of the patient,
   a hepatic flexure region of the patient,
   a transverse colon region of the patient,
   a splenic flexure region of the patient,
   a descending colon region of the patient,
   a sigmoid colon region of the patient, and
   a rectum region of the patient.

8. The method of claim 1, wherein the compression is temporarily maintained.

9. The method of claim 8, wherein the compression is removed and reapplied to the abdomen.

10. The method of claim 8, wherein focused compression is initially applied to a first region of the abdomen and is reapplied to a second region of the abdomen different than the first region.

11. The method of claim 10, wherein the focused compression is initially applied to the first region to improve visualization of a first part of a colon during the withdrawal process, and the second region of the abdomen is compressed to improve visualization of a second part of the colon different from the first part of the colon.

12. The method of claim 8, wherein compression is reapplied to the same region of the abdomen.

13. The method of claim 1, further comprising:
   applying focused compression to a portion of the abdomen.

14. The method of claim 13, wherein the focused compression is a compression focused on the transverse colon of the patient.

15. The method of claim 1, wherein maintaining compression of the abdomen of the patient during withdrawal of an endoscope is used to improve visualization of at least a portion of the colon.

16. The method of claim 1, wherein the compression of the abdomen of the patient is maintained while examining the lining of the colon during a withdrawal phase of an endoscopy procedure.

* * * * *